United States Patent
Wolfson

(10) Patent No.: US 10,702,412 B2
(45) Date of Patent: Jul. 7, 2020

(54) ORTHOPEDIC JOINT HINGE, METHODS AND DEVICES

(75) Inventor: Nikolaj Wolfson, San Francisco, CA (US)

(73) Assignee: Nikolaj Wolfson, San Francisco, CA (US)

( * ) Notice: Subject to any disclaimer, the term of this patent is extended or adjusted under 35 U.S.C. 154(b) by 0 days.

(21) Appl. No.: 13/308,238

(22) Filed: Nov. 30, 2011

(65) Prior Publication Data
US 2012/0143189 A1   Jun. 7, 2012

Related U.S. Application Data

(60) Provisional application No. 61/418,122, filed on Nov. 30, 2010.

(51) Int. Cl.
| | | |
|---|---|---|
| *A61B 17/00* | (2006.01) | |
| *A61F 5/01* | (2006.01) | |
| *A61B 17/60* | (2006.01) | |
| *A61B 17/56* | (2006.01) | |
| *A61H 1/02* | (2006.01) | |

(52) U.S. Cl.
CPC ............ *A61F 5/0125* (2013.01); *A61F 5/013* (2013.01); *A61B 17/60* (2013.01); *A61B 2017/567* (2013.01); *A61F 2005/0167* (2013.01); *A61H 1/024* (2013.01)

(58) Field of Classification Search
CPC ........ A61B 17/64–6491; A61B 2017/564–568
USPC ........ 602/16, 26; 606/53, 87–89; 623/18.11, 623/20.11–20.15, 20.24, 21.15–21.17, 623/23.39
See application file for complete search history.

(56) References Cited

U.S. PATENT DOCUMENTS

| | | | | | |
|---|---|---|---|---|---|
| 2,362,383 | A | * | 11/1944 | Lendinara | 403/58 |
| 2,696,817 | A | * | 12/1954 | Prevo | 623/20.12 |
| 3,466,669 | A | * | 9/1969 | Flatt | A61F 2/4241 |
| | | | | | 623/21.17 |
| 3,996,624 | A | * | 12/1976 | Noiles | 623/20.24 |
| 4,001,896 | A | * | 1/1977 | Arkangel | 623/20.24 |
| 4,911,719 | A | * | 3/1990 | Merle | 623/23.39 |

(Continued)

OTHER PUBLICATIONS

Morrey, Bernard F., M.D., "Treatment of Elbow Arthritis Distraction Arthroplasty," [online], [retrieved on May 12, 2010]. Retrieved from the Internet <URL: http://www.vjortho.com/1995/08/treatment-of-elbow-arthritis-distraction-arthroplasty/>.

(Continued)

*Primary Examiner* — Nicholas J Plionis
*Assistant Examiner* — Steven J Cotroneo
(74) *Attorney, Agent, or Firm* — Lowenstein Sandler LLP

(57) ABSTRACT

An orthopedic joint hinge assembly includes a first elongated member, a first coupler attached to the first elongated member and including a first interface surface, a second elongated member, and a second coupler attached to the second elongated member and including a second interface surface. Each of the first and second couplers is constrained to rotate about an axis of rotation. The first and second interface surfaces are offset from the axis of rotation and engage each other to block a relative rotation between the first and second members in a first direction and separate from each other to permit a relative rotation in an opposite direction.

6 Claims, 6 Drawing Sheets

(56) References Cited

U.S. PATENT DOCUMENTS

| | | | | |
|---|---|---|---|---|
| 5,938,700 | A * | 8/1999 | Lippincott, III | A61F 2/4241 |
| | | | | 623/21.15 |
| 6,475,242 | B1 * | 11/2002 | Bramlet | A61B 17/1659 |
| | | | | 623/21.11 |
| 6,540,708 | B1 * | 4/2003 | Manspeizer | 602/16 |
| 7,553,289 | B2 * | 6/2009 | Cadichon | 602/23 |
| 2008/0033566 | A1 * | 2/2008 | Berelsman et al. | 623/20.12 |
| 2010/0256543 | A1 * | 10/2010 | McCune | 602/16 |

OTHER PUBLICATIONS

Volkov, M.V., M.D. and O.V. Oganesyan, M.D., "Treatment of Fractures in Tubular Bones by the Volkov-Oganesyan Repositioning-Compression Apparatus," *Clinical Orthopaedics and Related Research*, Issue 186, pp. 195-201 (1984).

* cited by examiner 100 (cont.)

```
┌─────────────────────────────────────────────────────────────────┐
│ RESTRAINING THE FIRST AND SECOND ELONGATED COMPONENTS TO        │
│ ROTATE ABOUT THE AXIS OF ROTATION BY USING A COUPLING SHAFT     │
│ DISPOSED WITHIN BORES OF THE FIRST AND SECOND ELONGATED         │
│ COMPONENTS - 112                                                │
└─────────────────────────────────────────────────────────────────┘
                                │
┌─────────────────────────────────────────────────────────────────┐
│ PROGRESSIVELY INHIBITING A RELATIVE ROTATION BETWEEN THE FIRST  │
│ AND SECOND ELONGATED COMPONENTS BY CONTACTING FIRST AND         │
│ SECOND CURVED SURFACES OF THE FIRST AND SECOND COMPONENTS,      │
│ THE FIRST AND SECOND CURVED SURFACES BEING ECCENTRIC TO THE     │
│ AXIS OF ROTATION - 114                                          │
└─────────────────────────────────────────────────────────────────┘
                                │
┌─────────────────────────────────────────────────────────────────┐
│ BLOCKING A RELATIVE ROTATION BETWEEN THE FIRST AND SECOND       │
│ ELONGATED COMPONENTS BY CONTACTING FIRST AND SECOND CURVED      │
│ SURFACES OF THE FIRST AND SECOND COMPONENTS, THE FIRST AND      │
│ SECOND CURVED SURFACES BEING ECCENTRIC TO THE AXIS OF           │
│ ROTATION - 116                                                  │
└─────────────────────────────────────────────────────────────────┘
                                │
┌─────────────────────────────────────────────────────────────────┐
│ ROTATING AN INPUT MEMBER ROTATIONALLY COUPLED TO THE FIRST      │
│ ELONGATED COMPONENT - 118                                       │
└─────────────────────────────────────────────────────────────────┘
```

*FIG. 6*

ORTHOPEDIC JOINT HINGE, METHODS AND DEVICES

CROSS-REFERENCES TO RELATED APPLICATIONS

This application claims the benefit of priority of U.S. Provisional Application No. 61/418,122, filed on Nov. 30, 2010, the full disclosure of which is incorporated herein by reference.

BACKGROUND

The present invention relates to orthopedic hinge assemblies and related methods and devices.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention relates to orthopedic hinge assemblies and related methods. A disclosed orthopedic hinge assembly includes first and second elongated members that are coupled via a hinge. The hinge is configured to limit the relative rotation of the first and second members. The first and second elongated members can be coupled with a patient on opposite sides of a joint of the patient (e.g., a finger joint) to support the joint while limiting the motion of the joint. Accordingly, during a course of medical treatment, therapeutic motion of the joint can be induced and undesired motions of the joint can be prevented, thereby reducing or preventing associated injury to the joint.

Thus in one aspect, an orthopedic joint hinge assembly is provided. The hinge assembly includes a first elongated member, a first coupler attached to the first member, a second member, and a second coupler attached to the second member. The first coupler is attached to the first elongated member and includes a first interface surface. The second coupler is attached to the second elongated member and includes a second interface surface. The first and second couplers are rotationally coupled to rotate about an axis of rotation. The first and second interface surfaces are offset from the axis of rotation and configured to engage each other to block a relative rotation between the first and second members in a first rotation direction about the axis of rotation and separate from each other to permit a relative rotation between the first and second members in a second rotation direction about the axis of rotation opposite to the first rotation direction.

In many embodiments, the first and second elongated members have constant cross sections. For example, the first elongated member and/or the second elongated member can have a circular cross section.

The first and second couplers have suitable external surfaces. For example, the first coupler can include a first outer planar surface perpendicular to the axis of rotation and a first inner planar surface perpendicular to the axis of rotation. The second coupler can include a second outer planar surface perpendicular to the axis of rotation and a second inner planar surface perpendicular to the axis of rotation. In many embodiments, the first inner surface interfaces with the second inner surface. The first coupler can include a first curved surface transverse to the first inner surface. The first curved surface is eccentric to the axis of rotation. The second coupler can include a second curved surface transverse to the second inner surface. The second curved surface is eccentric to the axis of rotation. The first and second curved surfaces can be configured to engage each other so as to progressively inhibit a relative rotation between the first and second members in the first direction about the axis of rotation. Alternatively, the first and second curved surfaces can be configured to engage each other to block a relative rotation between the first and second members in the first direction about the axis of rotation.

In many embodiments, the orthopedic joint hinge assembly includes a coupling shaft that rotationally couples the first coupler with the second coupler. The hinge assembly can include a first retention member coupled to a first end of the coupling shaft and a second retention member coupled to a second end of the coupling shaft opposite to the first end of the coupling shaft. In many embodiments, the first and second couplers are disposed between the first and second retention members.

In many embodiments, the orthopedic joint hinge assembly includes additional components related to coupling the first and second coupling members. For example, the hinge assembly can include a bushing disposed between the first coupler and the coupling shaft. The hinge assembly can include a screw engaging a threaded hole in the first coupler and the coupling shaft to rotationally fix the first coupler to the coupling shaft. The first retention member can be rotationally fixed to the first end of the coupling shaft so that rotation of the retention member induces rotation of the coupling shaft, which can induce rotation of the first coupling member relative to the second coupling member. In many embodiments, the coupling shaft has a shoulder that engages the bushing. And in many embodiments, the bushing extends beyond the first outer planar surface of the first coupler so that the first retention member is offset from the first outer planar surface of the first coupler.

In many embodiments, the orthopedic joint hinge assembly includes additional components configured to interface with a patient. For example, the hinge assembly can include a first interface assembly coupled to the first elongated member and configured to interface with a patient on a first side of a joint of the patient. The hinge assembly can include a second interface assembly coupled to the second elongated member and configured to interface with the patient on a second side of the joint of the patient opposite to the first side. In many embodiments, a position of the first interface assembly and/or the second interface assembly can be adjusted along the first and second elongated members, respectively. In many embodiments, the hinge assembly includes a first plurality of interface assemblies coupled to the first elongated member. Each of the first plurality of interface assemblies can be configured to interface with a patient on a first side of a joint of the patient. The hinge assembly can include a second plurality of interface assemblies coupled to the second elongated member. Each of the second plurality of interface assemblies can be configured to interface with the patient on a second side of the joint of the patient opposite to the first side.

In another aspect, a method is provided for constraining a joint of a patient. The method includes rotating a first elongated component of an orthopedic hinge assembly relative to a second elongated component of the orthopedic hinge assembly about an axis of rotation fixed relative to both the first and second elongated components; engaging interface surfaces of the first and second elongated components to block a relative rotation between the first and second elongated components in a first direction about the axis of rotation; separating the interface surfaces during a relative rotation between the first and second elongated components in a second direction about the axis of rotation opposite to the first direction; constraining a patient on a first side of a joint of the patient with a first interface assembly coupled to the first elongated component; and constraining the patient on a second side of the joint of the patient opposite to the first side with a second interface assembly coupled to the second elongated component.

In many embodiments, the method can include additional acts. For example, the method can include restraining the first and second elongated components to rotate about the axis of rotation by using a coupling shaft disposed within bores of the first and second elongated components. The method can include progressively inhibiting a relative rotation between the first and second elongated components by contacting first and second curved surfaces of the first and second couplers, the first and second curved surfaces being eccentric to the axis of rotation. The method can include blocking a relative rotation between the first and second elongated components by contacting first and second curved surfaces of the first and second couplers, the first and second curved surfaces being eccentric to the axis of rotation. The act of rotating the first elongated component relative to the second elongated component can include rotating an input member rotationally coupled to the first elongated component.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 6 lists optional acts of the method of FIG. 5, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The present invention relates to orthopedic hinge assemblies and related methods. The assemblies of the present invention can be used in conjunction with or in a variety of indications, such as joint cartilage regeneration, repair of cartilage damage, distraction arthroplasty, cartilage cell implantations, stem cell technology, implantations of autologous chondrocytes, and resurfacing arthroplasty with distraction arthroplasty.

In some embodiments, the orthopedic hinge assemblies of the present invention can be incorporated internally or externally to facilitate therapy for a joint, e.g., a knee joint, of a subject.

Figure 1:
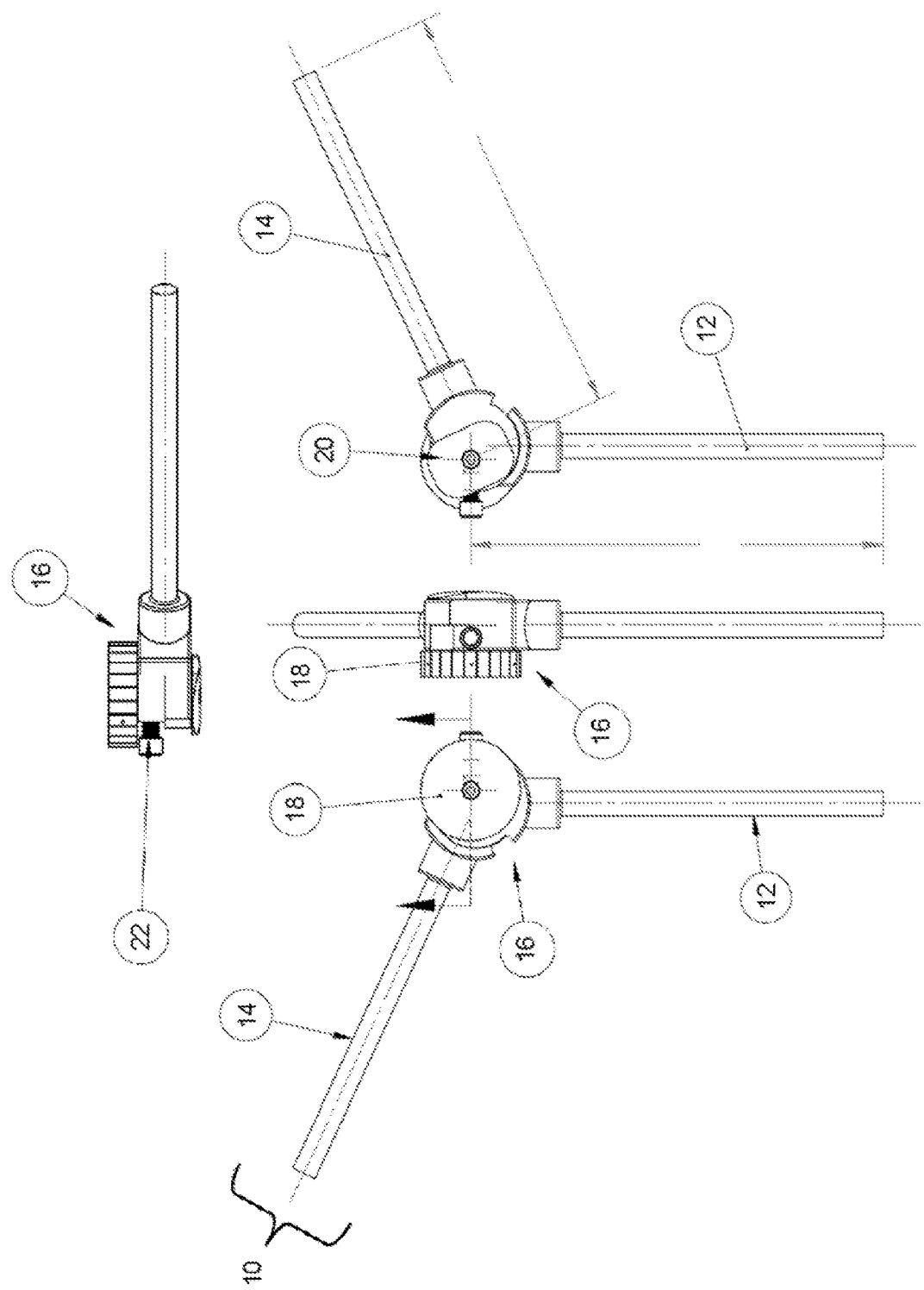
FIG. 1 illustrates top, back, and side views of an orthopedic hinge assembly, according to an exemplary embodiment.

FIG. 1 shows top, back, and side views of an orthopedic hinge assembly 10 in accordance with an exemplary embodiment of the present invention. The orthopedic hinge assembly 10 includes a first elongated component 12 and a second elongated component 14, which are coupled together at a joint assembly 16. The joint assembly 16 includes a wheel 18 and a washer 20. In many embodiments, the wheel 18 is rotationally tied to a coupling shaft used to rotationally couple the first elongated component 12 and the second elongated component 14 so that they rotate about an axis of rotation defined by the coupling shaft. As shown in the top view of the orthopedic hinge assembly 10, a screw 22 can be used to rotationally couple the coupling shaft to the first elongated component 12 so that the first elongated component 12 can be rotated relative to the second elongated component 14 by rotating the wheel 18. This ability to rotate the first elongated component 12 relative to the second elongated component 14 can be used, for example, for therapeutic purposes such as externally-driven articulation of a joint of a patient, thereby reducing the amount of patient generated internal stress on the joint.

Figure 2:
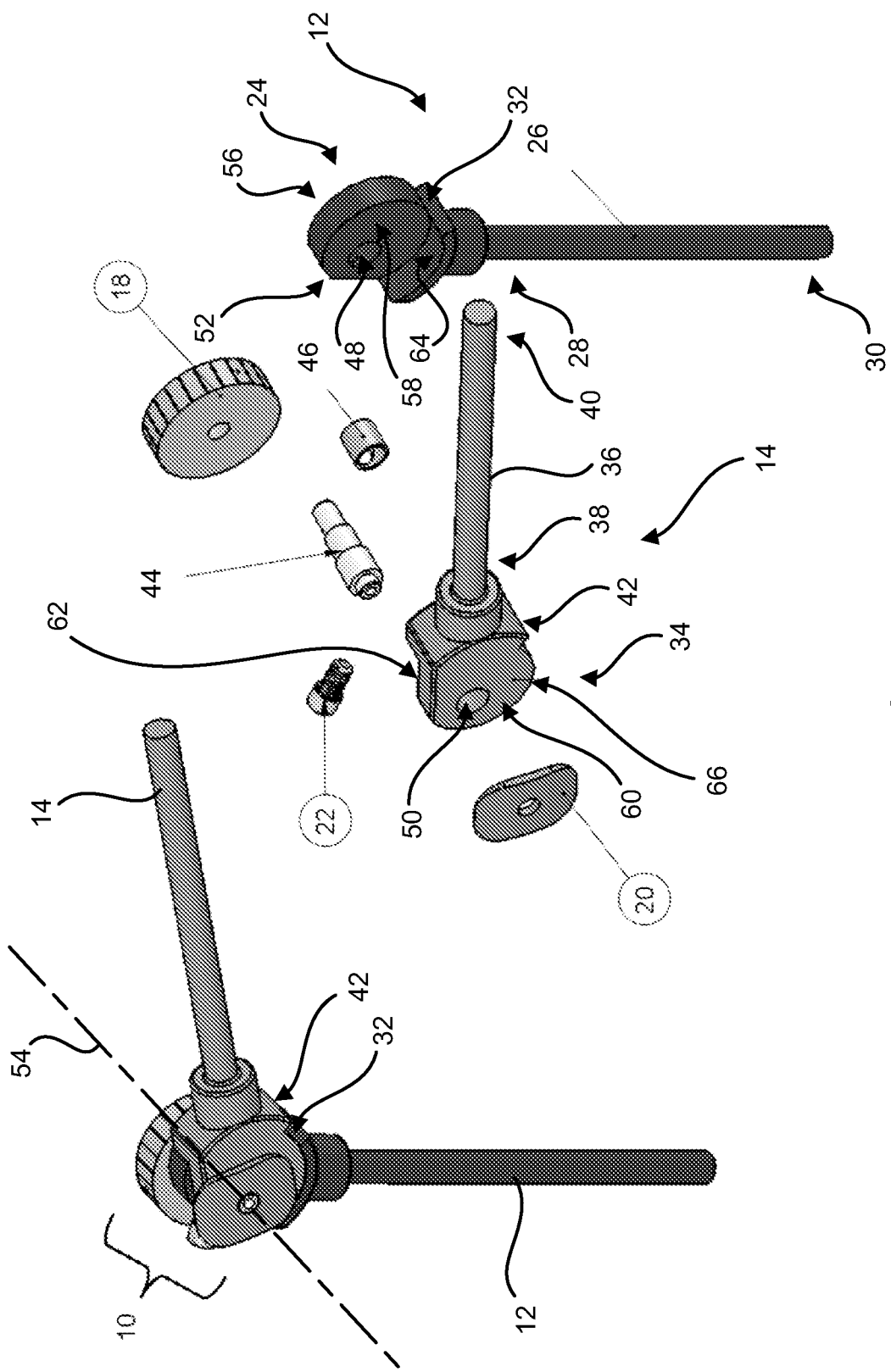
FIG. 2 shows a break out view of the orthopedic hinge assembly of FIG. 1 and its respective components.

FIG. 2 illustrates a break out view of the exemplary orthopedic hinge assembly 10. The first elongated component 12 includes a first coupler 24 and a first elongated member 26. The first elongated member 26 has a first end 28, a second end 30, and a constant circular cross-section there between. The first coupler 24 is attached to the first end 28 and includes a first interface surface 32. The second elongated member 14 includes a second coupler 34 and a second elongated member 36. The second elongated member 36 has a third end 38, a fourth end 40, and a constant circular cross-section there between. The second coupler 34 is attached to the third end 38 and includes a second interface surface 42. The joint assembly 16 includes the wheel 18, the washer 20, the screw 22, a coupling shaft 44, and a bushing 46. The first and second couplers 24, 34 have bores 48, 50, respectively, in which the coupling shaft 44 is disposed. The first coupler 24 has a threaded hole 52 through which the screw 22 engages the coupling shaft 44 through a hole in the bushing 46, thereby rotationally coupling the first elongated component 12 to the coupling shaft 24. The wheel 18 and the washer 20 are coupled with the coupling shaft 44 and retain the first and second couplers 24, 34 there between. The joint assembly 16 constrains the first and second couplers 24, 34 to rotate about an axis of rotation 54. The first and second interface surfaces 32, 42 are offset from the axis of rotation 54 and are configured to limit possible relative angular orientations between the first and second elongated components 12, 14. The first and second interface surfaces 32, 42 engage each other to block a relative rotation between the first and second elongated components 12, 14 in a first rotation direction about the axis of rotation 54. The first and second interface surfaces 32, 42 separate from each other to permit a relative rotation between the first and second elongated components 12, 14 in a second direction about the axis of rotation 54 opposite to the first direction. The first coupler 24 has a first outer planar surface 56 oriented perpendicular to the axis of rotation 54 and a first inner planar surface 58 also oriented perpendicular to the axis of rotation 54. Likewise, the second coupler 34 has a second outer planar surface 60 oriented perpendicular to the axis of rotation 54 and a second inner planar surface 62 also oriented perpendicular to the axis of rotation 54. The first inner surface 58 interfaces with the second inner surface 62.

The first and second couplers 24, 34 can be configured to progressively inhibit a relative rotation between the first and second elongated components 12, 14 about the axis of rotation 54 in the first angular direction. The first coupler 24 has a first curved surface 64 oriented transverse to the first inner surface 58. The first curved surface 64 is eccentric to the axis of rotation 54. The second coupler 34 has a second curved surface 66 oriented transverse to the second inner surface 62. The second curved surface 66 is also eccentric to the axis of rotation 54. When the first elongated component 12 rotates in the first direction relative to the second elongated component 14, the eccentricity of the first and second curved surfaces 64, 66 relative to the axis of rotation 54 results in increasing contact forces between the first and second couplers 24, 34 at the first and second curved surfaces 64, 66, thereby generating increased sliding friction and associated resistance to further rotation in the first direction. Contact between the first and second interface surfaces 32, 42 terminates further rotation in the first direction. Alternatively, the degree of eccentricity of the first and second curved surfaces 64, 66 relative to the axis of rotation 54 can be selected such contact between the first and second curved surfaces 64, 66 substantially blocks further relative rotation in the first direction.

Figure 3:
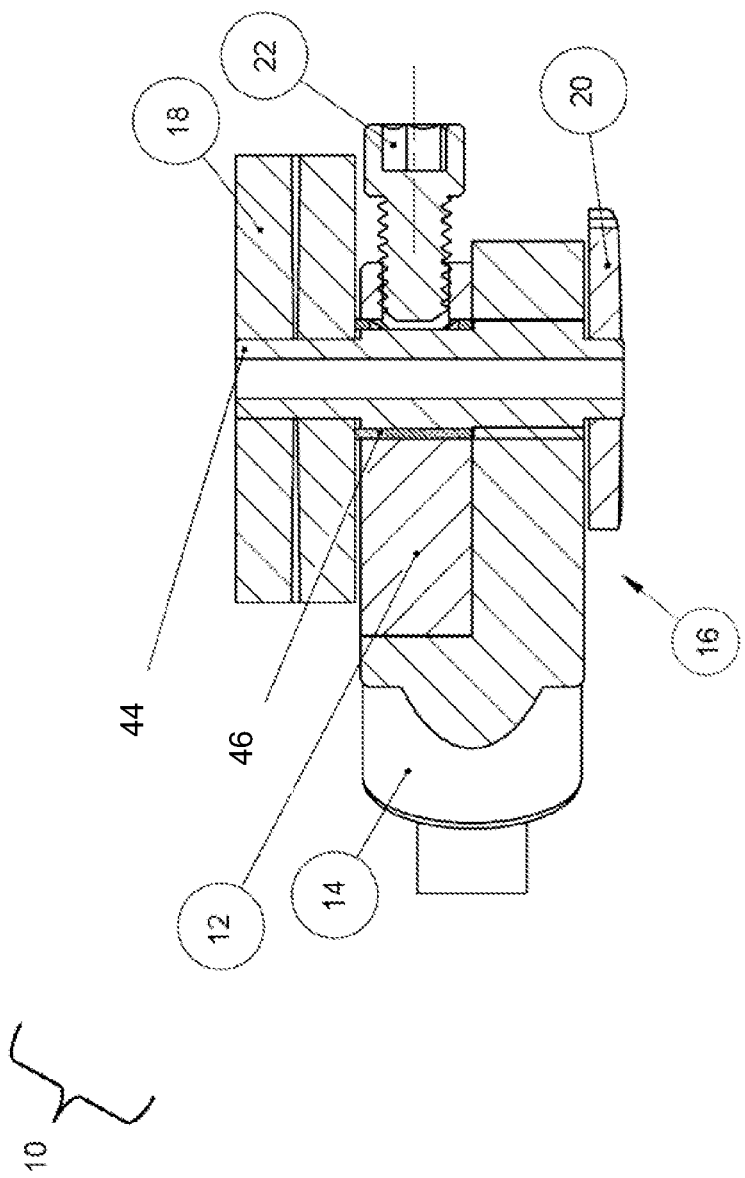
FIG. 3 shows a cross-sectional view of the orthopedic hinge assembly of FIG. 1.

FIG. 3 shows a cross-sectional view of the orthopedic hinge assembly 10. As shown, the coupling shaft 44 spans across the width of the hinge assembly 10 coupling the wheel 18 to the washer 20. The wheel 18 is rotationally coupled to the coupling shaft 44 so that rotating the wheel 18 rotates the coupling shaft 44. The bushing 46 surrounds the coupling shaft 44 and is disposed between the first elongated component 12 and the coupling shaft 44. The screw 22 is installed in a threaded hole in the first elongated component 12 and engages the coupling shaft 44, thereby rotationally coupling the first elongated component 12 to the coupling shaft 44.

Figure 4:
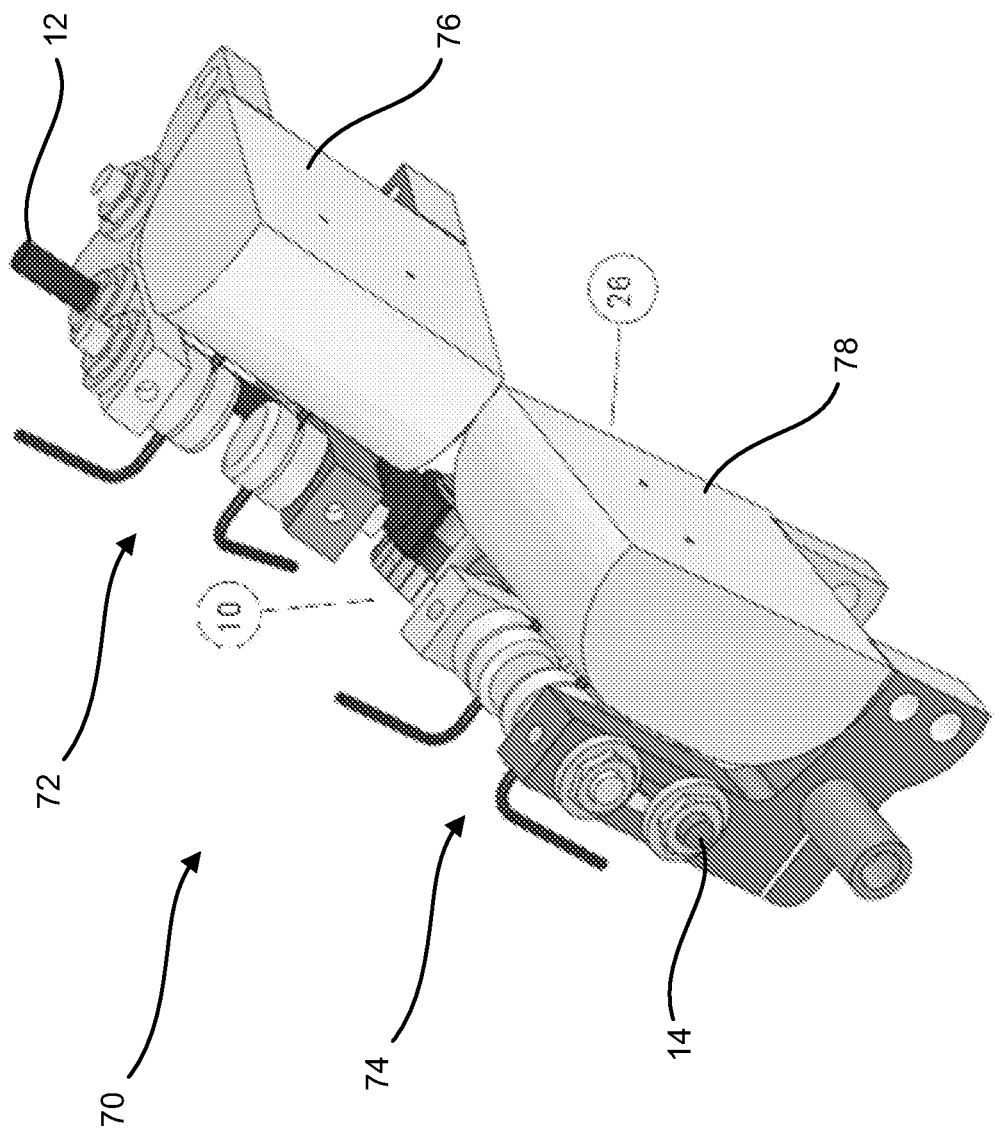
FIG. 4 illustrates a finger joint device incorporating the orthopedic hinge assembly of FIG. 1, in accordance with an exemplary embodiment.

FIG. 4 illustrates an exemplary device 70 incorporating the orthopedic hinge assembly 10. The device 70 includes the orthopedic hinge assembly 10, a first interface assembly 72 coupled to the first elongated component 12 and configured to interface with a patient on a first side of a joint of the patient, and a second interface assembly 74 coupled to the second elongated member 14 and configured to interface with the patient on a second side of the joint of the patient opposite to the first side. In FIG. 4, the first interface assembly 72 is shown interfacing with a first section 76 of a patient's finger on a first side of a finger joint (not shown) and the second interface assembly 74 is shown interfacing with a second section 78 of the patient's finger on a second side of the finger joint. In many embodiments, a position of each of the first and second interface assemblies 72, 74 can be adjusted along the first and second elongated components 12, 14. More than one interface assembly can be coupled with one or both of the first and second elongated components 12, 14.

Figure 5:
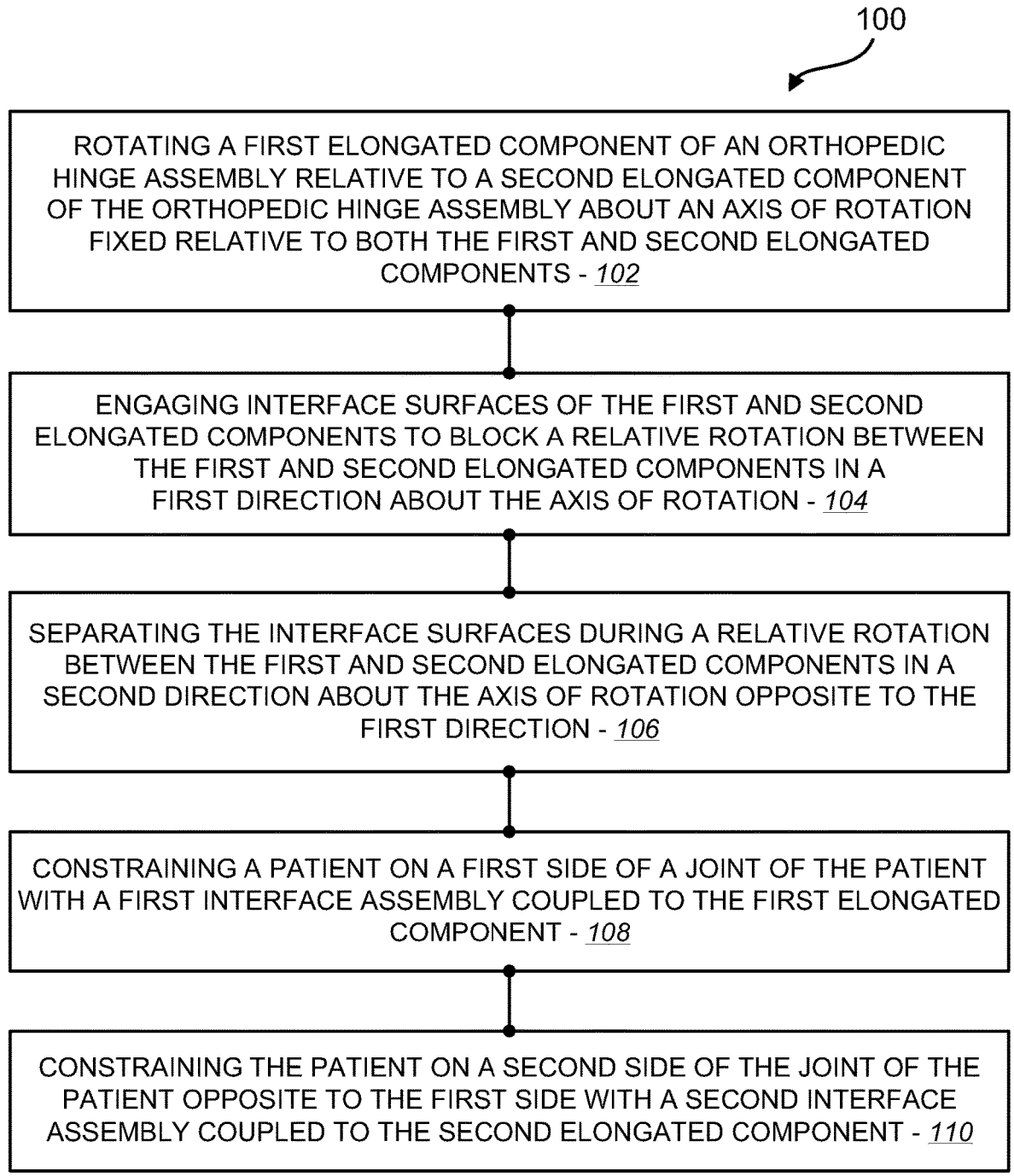
FIG. 5 is a simplified diagram of acts of a method for constraining a joint of a patient, in accordance with an exemplary embodiment.

FIG. 5 is a simplified diagram illustrating acts of a method 100 for constraining a joint of a patient, in accordance with many embodiments. Any suitable orthopedic joint hinge assembly, such as, but not limited to, the orthopedic joint hinge assembly 10 described herein can be used to practice the method 100. In act 102, a first elongated component of an orthopedic hinge assembly is rotated relative to a second elongated component of the orthopedic hinge assembly about an axis of rotation fixed relative to both the first and second elongated components. In act 104, interface surfaces of the first and second elongated components engage to block a relative rotation between the first and second elongated components in a first direction about the axis of rotation. In act 106, the interface surfaces separate during a relative rotation between the first and second elongated components in a second direction about the axis of rotation opposite to the first direction. In act 108, a patient on a first side of a joint of the patient is constrained with a first interface assembly coupled to the first elongated component. In act 110, the patient on a second side of the joint of the patient opposite to the first side is constrained with a second interface assembly coupled to the second elongated component.

FIG. 6 is a simplified diagram illustrating optional acts of the method 100, in accordance with many embodiments. In optional act 112, the first and second elongated components are restrained to rotate about the axis of rotation by using a coupling shaft disposed within bores of the first and second elongated components. In optional act 114, a relative rotation between the first and second elongated components is progressively inhibited by contacting first and second curved surfaces of the first and second components. The first and second curved surfaces are eccentric to the axis of rotation. In optional act 116, a relative rotation between the first and second elongated components is blocked by contacting the first and second curved surfaces of the first and second components. In optional act 118, an input member rotationally coupled with the first elongated component is rotated.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An orthopedic joint hinge assembly comprising:
a first cylindrical elongated member;
a first coupler attached to the first cylindrical elongated member and including a first interface surface;
a second cylindrical elongated member;
a second coupler attached to the second cylindrical elongated member and including a second interface surface;
each of the first and second couplers being constrained to rotate about an axis of rotation, the first and second interface surfaces being offset from the axis of rotation and configured to engage each other to block a relative rotation between the first and second cylindrical elongated members in a first direction about the axis of rotation and separate from each other to permit a relative rotation between the first and second cylindrical elongated members in a second direction about the axis of rotation opposite to the first direction, wherein the each of the first and second cylindrical elongated member has a constant circular cross section along an entire length of the respective first and second cylindrical elongated member, wherein:
the first coupler comprises a first outer planar surface perpendicular to the axis of rotation and a first inner planar surface perpendicular to the axis of rotation,
the second coupler comprises a second outer planar surface perpendicular to the axis of rotation and a second inner planar surface perpendicular to the axis of rotation,
the first inner planar surface to interface with the second inner planar surface,
the first coupler further comprises a first curved surface transverse to the first inner planar surface, the first curved surface being eccentric to the axis of rotation,
the second coupler further comprises a second curved surface transverse to the second inner planar surface,
the second curved surface being eccentric to the axis of rotation, wherein the axis of rotation is offset from a first center with respect to the first curved surface of the first inner planar surface and a second center with respect to the second curved surface of the second inner planar surface, and
the first and second curved surfaces are configured to contact each other so as to progressively inhibit a relative rotation between the first and second cylindrical elongated members in the first direction about the axis of rotation;
a coupling shaft to rotationally couple the first coupler with the second coupler
a first retention member to couple to a first end of the coupling shaft;
a second retention member to couple to a second end of the coupling shaft opposite to the first end of the coupling shaft, the first and second couplers being disposed between the first and second retention members; and
a screw to engage a threaded hole in the first coupler and the coupling shaft through a hole in a bushing to rotationally fix the first coupler to the coupling shaft.

2. The orthopedic joint hinge assembly of claim 1, wherein the first retention member is rotationally fixed to the first end of the coupling shaft.

3. The orthopedic joint hinge assembly of claim 1, further comprising:
a first interface assembly coupled to the first cylindrical elongated member and configured to interface with a patient on a first side of a joint of the patient; and
a second interface assembly coupled to the second cylindrical elongated member and configured to interface with a patient on a second side of the joint of the patient opposite to the first side.

4. The orthopedic joint hinge assembly of claim 3, wherein a position of each of the first and second interface assemblies can be adjusted along the first and second cylindrical elongated members, respectively.

5. The orthopedic joint hinge assembly of claim 1, further comprising a first plurality of interface assemblies coupled to the first cylindrical elongated member, each of the first plurality of interface assemblies configured to interface with a patient on a first side of a joint of the patient.

6. The orthopedic joint hinge assembly of claim 5, further comprising a second plurality of interface assemblies coupled to the second cylindrical elongated member, each of the second plurality of interface assemblies configured to interface with the patient on a second side of the joint of the patient opposite to the first side.

* * * * *